(12) United States Patent
Moffarah (10) Patent No.: US 12,383,711 B2
(45) Date of Patent: Aug. 12, 2025

(54) INFLATABLE MEDICAL BALLOON WITH S-SHAPED FIBER

(71) Applicant: C.R. Bard, Inc., Tempe, AZ (US)

(72) Inventor: Meir Moffarah, Sacramento, CA (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 986 days.

(21) Appl. No.: 17/264,118

(22) PCT Filed: Aug. 24, 2018

(86) PCT No.: PCT/US2018/047946
§ 371 (c)(1),
(2) Date: Jan. 28, 2021

(87) PCT Pub. No.: WO2020/040790
PCT Pub. Date: Feb. 27, 2020

(65) Prior Publication Data
US 2021/0299415 A1    Sep. 30, 2021

(51) Int. Cl.
*A61M 25/10* (2013.01)
*B29C 70/30* (2006.01)

(52) U.S. Cl.
CPC .... *A61M 25/1029* (2013.01); *A61M 25/1002* (2013.01); *A61M 25/104* (2013.01); *A61M 2025/1031* (2013.01); *A61M 2025/1075* (2013.01); *A61M 2025/1084* (2013.01); *B29C 70/30* (2013.01)

(58) Field of Classification Search
CPC .......... A61M 25/1029; A61M 25/1002; A61M 25/104; A61M 2025/1031; A61M 2025/1075; A61M 2025/1084
See application file for complete search history.

(56) References Cited

U.S. PATENT DOCUMENTS

| | | | |
|---|---|---|---|
| 6,841,213 B2 * | 1/2005 | Parsonage | A61M 25/104 427/2.24 |
| 2010/0318029 A1 * | 12/2010 | Pepper | A61M 25/10 604/103.07 |
| 2011/0172698 A1 * | 7/2011 | Davies, Jr. | D04C 1/06 29/428 |
| 2015/0297871 A1 | 10/2015 | Aggerholm | |
| 2018/0193609 A1 | 7/2018 | Lally et al. | |

FOREIGN PATENT DOCUMENTS

| | | |
|---|---|---|
| EP | 2932997 A1 | 10/2015 |
| JP | 2015518776 A | 7/2015 |
| WO | 2014176422 A1 | 10/2014 |

* cited by examiner

*Primary Examiner* — Dung T Ulsh
(74) *Attorney, Agent, or Firm* — Dickinson Wright PLLC; Andrew D. Dorisio (57) ABSTRACT

A fiber-reinforced device (100), such as an inflatable medical balloon, includes a cylindrical central portion. The balloon includes (100) first and second tapered portions connected to the cylindrical central portion along a longitudinal axis extending from a first end of the balloon to a second end of the balloon. The balloon includes at least one fiber (134, 142) having a fixed, S-shaped portion in a plan view, the fixed S-shaped portion remaining intact when the inflatable balloon is fully inflated.

9 Claims, 4 Drawing Sheets

INFLATABLE MEDICAL BALLOON WITH S-SHAPED FIBER

INCORPORATION BY REFERENCE

All publications and patent applications mentioned in this specification are herein incorporated by reference to the same extent as if each individual publication or patent application was specifically and individually indicated to be incorporated by reference.

BACKGROUND

Fiber based devices and expandable devices, such as balloons, are widely used in medical procedures. In the case of a balloon, it is inserted, typically on the end of a catheter, until the balloon reaches the area of interest. Adding pressure to the balloon causes the balloon to inflate. In one variation of use, the balloon creates a space inside the body when the balloon inflates.

Balloons may be used in the heart valves, including during Balloon Aortic Valvuloplasty (BAV) and Transcatheter Aortic Valve Implantation (TAVI). The balloons can be used to open a stenosed aortic valve. A stenosed valve may have hard calcific lesions which may tend to tear or puncture a balloon. Additionally, a precise inflated balloon diameter may be desired for increased safety and control.

Balloons may be used to move plaque away from the center of a vascular lumen toward the vasculature walls, such as during an angioplasty or a peripheral vasculature procedure. During this procedure, a balloon tipped catheter is placed in a vascular obstruction. As the balloon is inflated, the vessel constriction is dilated, resulting in improved blood flow.

Two basic types of balloons are utilized: One is a high pressure, low-compliance balloon. The other is a lower pressure, high-compliance balloon.

High-compliance medical balloons are often composed of urethane, latex, silicone, PVC, Pebax, and other elastomers. As the pressure in a high-compliant balloon is increased, the balloon dimensions expand. Once the pressure is reduced, the high-compliance medical balloon may return to its original shape, or near its original shape. High-compliance medical balloons can easily expand several times in volume between zero inflation pressure and burst.

Traditional high-compliance medical balloons can be inadequate for many reasons. High-compliance, or highly elastic medical balloons typically cannot reach high pressures because their walls have a low tensile strength and their walls thin out as the balloon expands. In some instances, high-compliance medical balloons provide insufficient force to complete a procedure. Exceeding the rated pressure of a high-compliance medical balloon creates an excessive risk of balloon failure which can lead to serious complications for the patient. Moreover, high-compliance medical balloons also have poor shape control. As a high-compliance medical balloon expands, it may assume a shape dictated mostly by the particulars of the environment inside the patient rather than the clinical goals. In some cases, this can be contrary to what the medical practitioner desires. Many medical procedures are predicated on forming a particular balloon shape reliably. Further, high-compliance medical balloons often suffer from poor puncture and tear resistance.

Low-compliance, high pressure medical balloons substantially retain their shape under comparatively high pressures. PET (polyethylene terephthalate) is the most common material for use in high pressure low-compliance balloons. PET is commonly used for high-performance angioplasty balloons. PET is stronger than other polymers, can be molded into a variety of shapes and can be made very thin (e.g., 5 µm to 50 µm (0.0002 in. to 0.002 in.)), thus giving these balloons a low profile. However, balloons made from PET walls are fragile and prone to tears. When pressed against a hard or sharp surface in the body, such as stenosis, PET balloons have poor puncture resistance. PET is very stiff so balloons made from PET may be difficult to pack or fold into a small diameter and may have poor trackability (i.e., the ability to slide and bend over a guidewire deployed through a tortuous vessel). Further, balloons made from PET, while stronger than most other balloons made from homogenous polymers, may still not be strong enough to hold pressures sufficient to complete certain medical procedures. Additionally, with a large balloon diameter (For example, 20 mm or greater), a PET balloon still has excessive compliance for procedures such as BAV and TAVI. Nylon balloons are an alternative material for low-compliance, high pressure balloons. However, these nylon balloons are typically weaker than PET balloons and so can contain less pressure. Nylon readily absorbs water, which can have an adverse effect on Nylon's material properties in some circumstances. Nylon has improved puncture resistance over PET and is more flexible than PET.

Fiber-reinforced composite balloons are another alternative low-compliance, high pressure medical balloon. Such fiber-reinforced composite balloons can advantageously sustain high pressures, provided precise shape control, and are highly resistant to tear and puncture. The manufacturing process for fiber-reinforced balloons, however, can be complicated and expensive, requiring the application of multiple different layers of fibers in order to achieve the desired support. Often, at least one of these layers consists of a fabric de-convolution pattern layer wrapped around a base balloon. Such forming and wrapping of the fabric pattern layer can be cumbersome, labor and equipment intensive, and time consuming. Further, depending upon the orientation of the fibers, the tear pattern of a fiber-reinforced balloon (sometimes referred to as its "rip" or "rip-stop" properties) upon bursting can result in enhanced difficulties in removing the balloon through a shaft.

Thus, there exists the need to create a fiber-reinforced device, such as a balloon, that can be manufactured quickly and easily, with a low profile and enhanced trackability, while still maintaining its ability to withstand high pressures, provide precise shape control, and have highly controlled tear properties.

SUMMARY OF THE DISCLOSURE

One object of the invention is thus to create a fiber-reinforced device, such as a balloon, that can be manufactured quickly and easily, with a low profile and enhanced trackability, while still maintaining its ability to withstand high pressures, provide precise shape control, and have highly controlled tear properties.

In general, in one embodiment, this object is achieved by a medical apparatus comprising an inflatable balloon, which may be non-compliant, including at least one fiber having a portion with an S-shape in a plan view, the S-shape remaining when the inflatable balloon is fully inflated. In some embodiments, the inflatable balloon comprises a generally cylindrical portion and first and second tapered portions connected to the generally cylindrical portion. In some embodiments, only the generally cylindrical portion includes the at least one fiber having the S-shaped portion, and in other embodiments, only the first or second tapered portion includes the at least one fiber having the S-shaped portion.

The at least one fiber may comprise a hoop fiber extending in a circumferential direction. The at least one fiber may comprise a longitudinal fiber extending generally parallel to a longitudinal axis of the inflatable balloon. The at least one fiber may comprise a first hoop fiber extending in a circumferential direction, and further including a longitudinal fiber extending generally parallel to a longitudinal axis, the longitudinal fiber also having an S-shaped portion. The at least one fiber may include a generally linear portion connected to the S-shaped portion. The at least one fiber may be fixedly attached to a base balloon by an adhesive.

In accordance with a further aspect of the disclosure, a medical apparatus comprises an inflatable balloon including a generally cylindrical portion and first and second tapered portions connected to the generally cylindrical portion, and at least one fiber including a first portion having an S-shape, the first portion extending only along the generally cylindrical portion of the inflatable balloon. The at least one fiber may include a second, linear portion extending along one of the first or second tapered portions of the inflatable balloon. The at least one fiber may comprise s a hoop fiber extending in a circumferential direction. The at least one fiber may comprise a longitudinal fiber extending generally parallel to a longitudinal axis of the inflatable balloon. The at least one fiber may comprise a first hoop fiber extending in a circumferential direction, and further including a longitudinal fiber extending generally parallel to a longitudinal axis, the longitudinal fiber also having an S-shaped portion.

This disclosure also pertains to a method of forming a medical apparatus, the method comprising fixing at least one fiber having an S-shaped portion in a plan view to an inflatable balloon, the S-shaped portion retaining an S-shape when the inflatable balloon is fully inflated. The fixing step may comprise adhesively attaching the fiber to a base balloon. The fixing step may comprise fixing the S-shaped portion of the at least one fiber only along a generally cylindrical portion of the inflatable balloon. The fixing step may be completed during a step of applying the at least one fiber.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Referring now to the drawings, wherein like reference numbers are used herein to designate like elements throughout, the various views and embodiments of semi-compliant medical balloons are illustrated and described, and other possible embodiments are described. The Figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Figure 1:
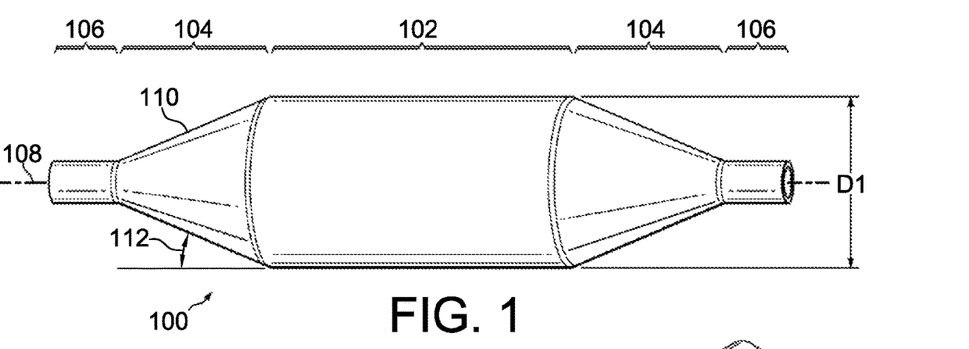
FIG. 1 shows an inflatable balloon in a fully inflated condition.

FIG. 1 is a side view of a fiber-reinforced medical dilation balloon according to one embodiment. As illustrated, medical balloon 100 is shown in a fully inflated state, as indicated by dimension D1 indicative of outer diameter, which in the case of a non-compliant balloon, means that the further introduction of fluid under pressure to the interior compartment of the balloon does not result in any meaningful change to this dimension. Balloon 100 includes a generally cylindrical or barrel portion 102 disposed between tapered cone portions 104 and cylindrical neck portions 106 extending from the cone portions along a longitudinal axis 108 of the balloon. The outer surface 110 of the cone portion 104 forms an angle 112 (the "cone angle") with respect to a longitudinal extension of the wall of the barrel portion 102. Higher cone angles generally provide a shorter total balloon length. In some embodiments, balloon 100 may have a cone angle 112 in the range of 12 degrees to 22 degrees, in others from 18 degrees to 22 degrees. In some embodiments, the cone angle 112 is about 20 degrees.

Figure 2:
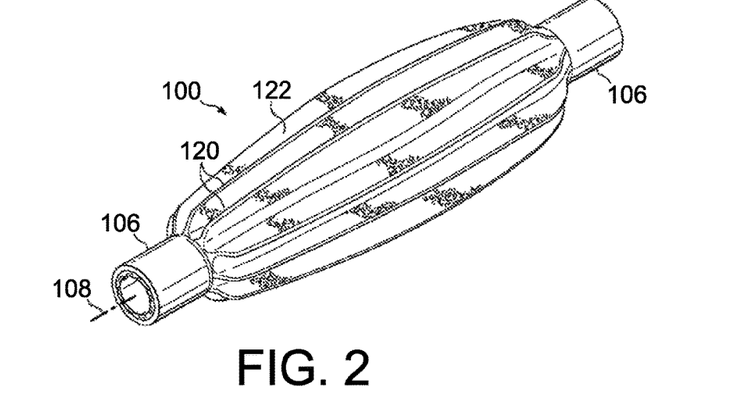
FIG. 2 shows an inflatable balloon in a folded condition.

Referring to FIG. 2, balloon 100 is illustrated in a deflated state. In its deflated state, the walls of barrel portion 102 and cone portions 104 of balloon 100 form pleats or folds 120 with creases 122 between the folds. As illustrated, folds 120 extend longitudinally from one neck portion 106 to the opposing neck portion 106. The pleated construction of the cone and barrel sections, 104, 106 reduces the diameter of balloon 100 to facilitate insertion of the balloon in its deflated state. Once positioned at the desired location, balloon 100 may be inflated through a catheter with a pressurized fluid such as a saline solution. As the balloon 100 is inflated, folds and creases 120, 122 substantially disappear as the balloon reaches a fully inflated size having a nominal diameter D1 as illustrated in FIG. 1.

As noted above, the balloon 100 may be non-compliant, which means that further increases in the pressure of the fluid used to inflate the balloon (i.e., beyond the pressure needed to reach the nominal diameter D1) do not result in further meaningful expansion. However, certain aspects of this disclosure may be applicable to semi-compliant or compliant balloons, and so it should not be considered limited to only non-compliant balloons. While balloon 100 may be constructed to any dimensions, balloons having a deflated diameter in the range from about 4 French Units (i.e., about 0.053 inches or 1.35 millimeters) to about 12 French Units (i.e., about 0.158 inches or 4.0 millimeters) are useful in the fields of cardiology, radiology, orthopedics and urology. In one embodiment, balloon 100 has a deflated diameter in the range of 4 to 12 French Units and a folded (e.g. when the balloon is deflated) wall thickness of from about 0.0010 to about 0.0060 inches.

Figures 3, 4:
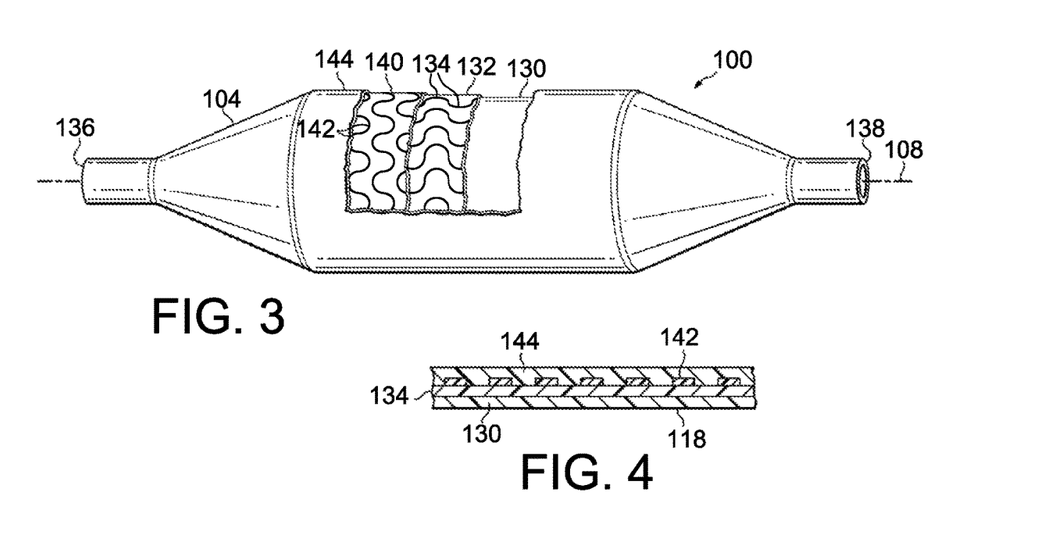
FIG. 3 is a partial cutaway view of the balloon of FIG. 1.
FIG. 4 is a partial longitudinal cross-section through the barrel wall of the balloon of FIG. 1.

FIG. 3 is a partial-sectional view of balloon 100, further illustrating the structure of the balloon. In one embodiment, balloon 100 includes a base layer or base balloon 130. Base balloon 130 is formed from a suitable polymer such as a nylon or a polyether block amide (PEBA) such as PEBAX® brand PEBA having a Shore D hardness from about 25 to about Shore D 54. In one embodiment, base balloon 130 has a double wall thickness of from about 0.0012 inches to about 0.0016 inches. Positioned over base balloon 130 is a first fiber layer 132 including a plurality of longitudinally extending, inelastic fibers 134.

In one variation, fibers 134 are substantially the same length and extend from a first end 136 to a second end 138 of balloon 100. In other embodiments, fibers 134 may have different lengths. For example, one group of longitudinal fibers 134 may extend over the entire length of balloon 100 while another group of fibers may extend only over the length of barrel 102 or over the length of the barrel and partially over the conc. Longitudinally-oriented reinforcing fibers 134 may be oriented parallel or substantially parallel to one another and perpendicular within about 10 to 15 degrees to the balloon's longitudinal axis 108. In one embodiment, fibers 134 may be attached to base balloon 130 with a suitable adhesive, such as a polyurethane, a soluble, weldable polyamide material and/or embedded in a polymeric matrix and, as discussed below, will remain fixed in position as a result of such attachment.

The inelastic fibers used may be formed from a variety of materials. For instance, the fibers may comprise Kevlar, Vectran, Spectra, Dacron, Dyneema, Turlon (PBT), Zylon (PBO), polyimide (PIM) and ultrahigh molecular weight polyethylenes, or any combination thereof. In one variation, the inelastic reinforcing fiber may be a multi-filament Technora® brand paraphenylenc/3,4-oxydiphenylenc/terephthalamide copolymer.

In one embodiment, a second fiber layer 140 is positioned over first fiber layer 132, and includes one or more hoop or circumferential reinforcing fibers 142. In one variation, one continuous hoop fiber 142 is wound over first fiber layer 132 from first end 136 to second end 138 of balloon 100. Circumferential reinforcing fibers 142 may be parallel or substantially parallel to one another and perpendicular within about 15 degrees to the longitudinally-oriented reinforcing fibers 134. In other embodiments, the second fiber layer may comprise a woven, non-woven, knitted or braided fiber material. Fiber or fibers 142 may be secured in position with suitable adhesive such as a polyurethane, and/or embedded in a polymeric matrix.

In the illustrated embodiment, balloon 100 includes an outer layer 144. Outer layer 144 is optional, and may provide additional material to increase the puncture-resistance and surface smoothness of the balloon 100. Outer layer 144 may be formed from the same material as base balloon 130 or a different material. Outer layer 144 may be formed from a suitable polymer such as nylon or a polyether block amide, such as PEBAX® brand PEBA.

FIG. 4 is a partial longitudinal section of wall 118 of balloon 100 further illustrating construction of balloon 100. As illustrated, one or more of the longitudinal fibers 134 and hoop fibers 142 are fixed in position relative to the balloon 100 and have at least one S-shaped portion. As shown, this S-shaped portion may repeat continuously to create a serpentine or sinuosoidal fiber (meaning the fiber crosses the same imaginary axis of symmetry while curving in opposite directions on either side of the axis). This pattern of spaced S-shaped fibers, increases the amount of the surface area of the balloon 100 covered by each fiber pass in view of the repeating S-shape used, without increasing the number of fiber passes, and thus maintains a desired low profile and improved trackability (especially when the hoop fibers are S-shaped or serpentine, since the lower density of hoop fibers improves flexibility about the longitudinal axis for purposes of tracking through the vasculature).

Figure 5:
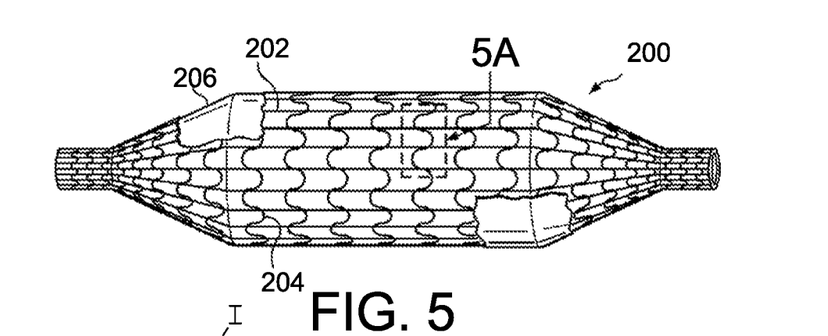
FIG. 5 illustrates the placement of hoop fibers having a serpentine configuration on a non-compliant medical balloon.
Figure 5A:
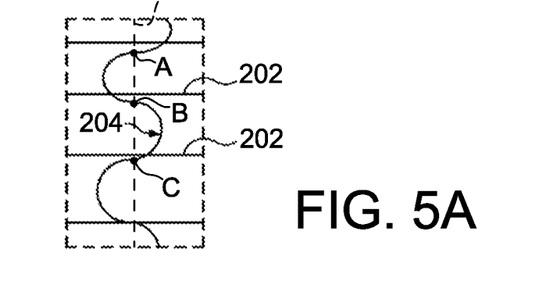
FIG. 5A is an enlarged view of a section of the balloon of FIG. 5.

As perhaps best understood from FIG. 5, one example of a balloon 200 including serpentine hoop fibers 204 with one or more S-shaped portions is shown. These hoop fibers 204 may overlie or underlie longitudinal fibers 202, which may be provided over a base balloon 206 and are fixed in position. The balloon 200 may be non-compliant, and shown in a fully inflated condition. Thus, as can be understood from FIG. 5A, the hoop fiber 204 retains the S-shape upon full inflation of the balloon 200, and such shape does not disappear as a result. In other words, the fiber 202 remains substantially attached to the base balloon 206 (and/or any underlying longitudinal fibers 202), and thus contributes to the burst strength of the balloon 200 over a greater surface area than a hoop fiber that does not include the S-shape.

The S-shaped portion of any fiber applied to the balloon 200 may have any desired amplitude in the corresponding direction in which the curve exists (circumferentially for the longitudinal fibers 134 and longitudinally for the hoop fibers 142, but in both cases, curved in a plan view when looking down on the balloon surface from above). Regardless of the desired amplitude, the fiber 134 or 142 crosses the same imaginary circumferential or longitudinal axis at least three times in view of the S-shaped portion (note imaginary axis I in FIG. 5A and crossover points A, B, and C), even when fully inflated. In the illustrated embodiments, in can be appreciated that adjacent fibers extending in the same direction (e.g., circumferentially) do not overlap with each other, which reduces the overall thickness of the fiber layer provided.

Figure 6:
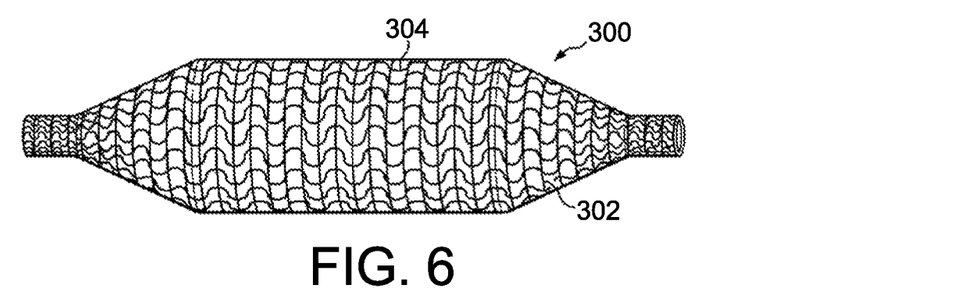
FIG. 6 illustrates the placement of longitudinal fibers having a serpentine configuration on a medical balloon.

The S-shaped portion(s) may also be provided on the longitudinal fibers, which are thus considered to have a sinusoidal or serpentine configuration. For example, as indicated in FIG. 6, a balloon 300 includes hoop fibers 302 that extend in the circumferential direction along a generally straight line or are linear, and longitudinal fibers 304 that include the repeating S-shaped portions. Again, the balloon 300 in FIG. 6 is non-compliant, and thus the longitudinal fibers 304 are fixed in place to fully retain their S-shaped configuration, despite the full inflation of the balloon 300.

Figure 7:
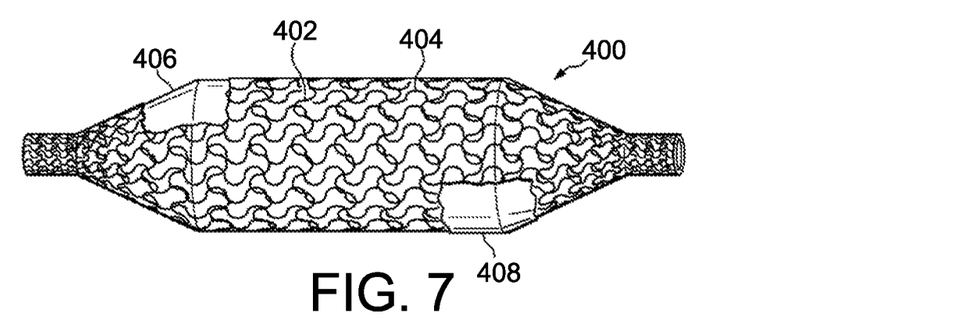
FIG. 7 illustrates the placement of both longitudinal and hoop fibers having a serpentine configuration on a medical balloon.

The S-shaped portion(s) may be provided for both the longitudinal and the hoop fibers. Thus, as indicated in FIG. 7, a balloon 400 may comprise S-shaped longitudinal fibers 402 and S-shaped hoop fibers 404. As in the above-embodiments, the fibers 402, 404 may be laid down onto a base balloon 406, which may be non-compliant such that the fibers retain their shape when the balloon 400 is fully inflated, as shown.

Figure 8:
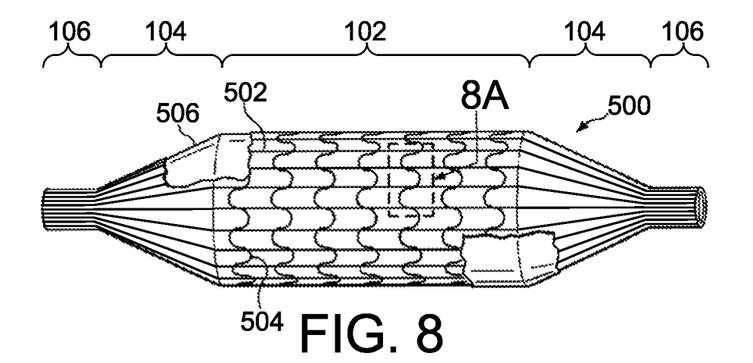
FIG. 8 illustrates the placement of hoop fibers having a serpentine configuration on only the working length of a medical balloon.
Figure 8A:
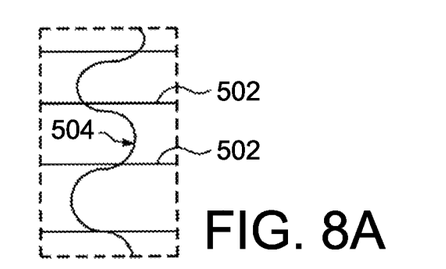
FIG. 8A is an enlarged view of a section of the balloon of FIG. 8.

The S-shaped fibers may be provided only along selected portions of the inflatable balloon. For instance, as shown in FIG. 8, S-shaped hoop fibers 504 may be provided along a barrel portion 102, but not along the conical or neck portions 104, 106 of the balloon 500, which may include the longitudinal fibers 502 (shown straight, but which also may be S-shaped, as noted above). As indicated in FIGS. 8-8A, the S-shaped fibers, such as hoop fibers 504, retain their shape on full inflation of the balloon 500. Reducing the fiber build up on the conical or tapered portions 104 (which tend to be thicker by virtue of the formation of the base balloon 506 by stretch blow molding) advantageously improves trackability.

Figure 9:
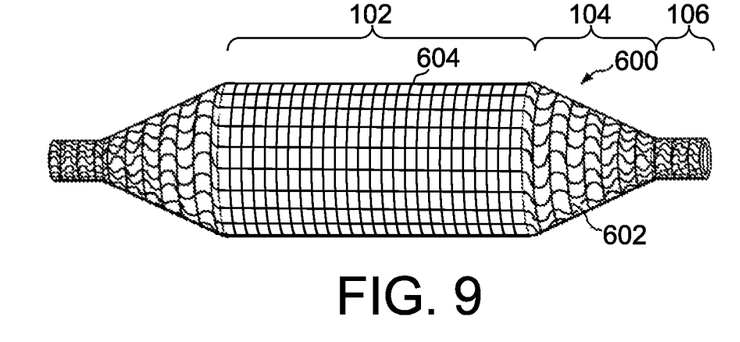
FIG. 9 illustrates the placement of longitudinal fibers having a partially linear configuration on the barrel portion and a serpentine configuration on the tapered portions of a medical balloon.

Likewise, the individual fibers may have variable shapes. For example, as shown in FIG. 9, the longitudinal fibers 602 of balloon 600 are S-shaped in the conical and neck portions 104, 106, but straight in the barrel portion 102. The division between straight and S-shaped portions need not be confined to particular defined portions of the balloon (e.g., the longitudinal fibers 602 could be straight along part of the barrel 102 or cone portions 104 and S-shaped along part of these portions). The S-shaped fibers may also overlap with straight fibers extending in the same direction along any portion of the balloon.

Figure 10:
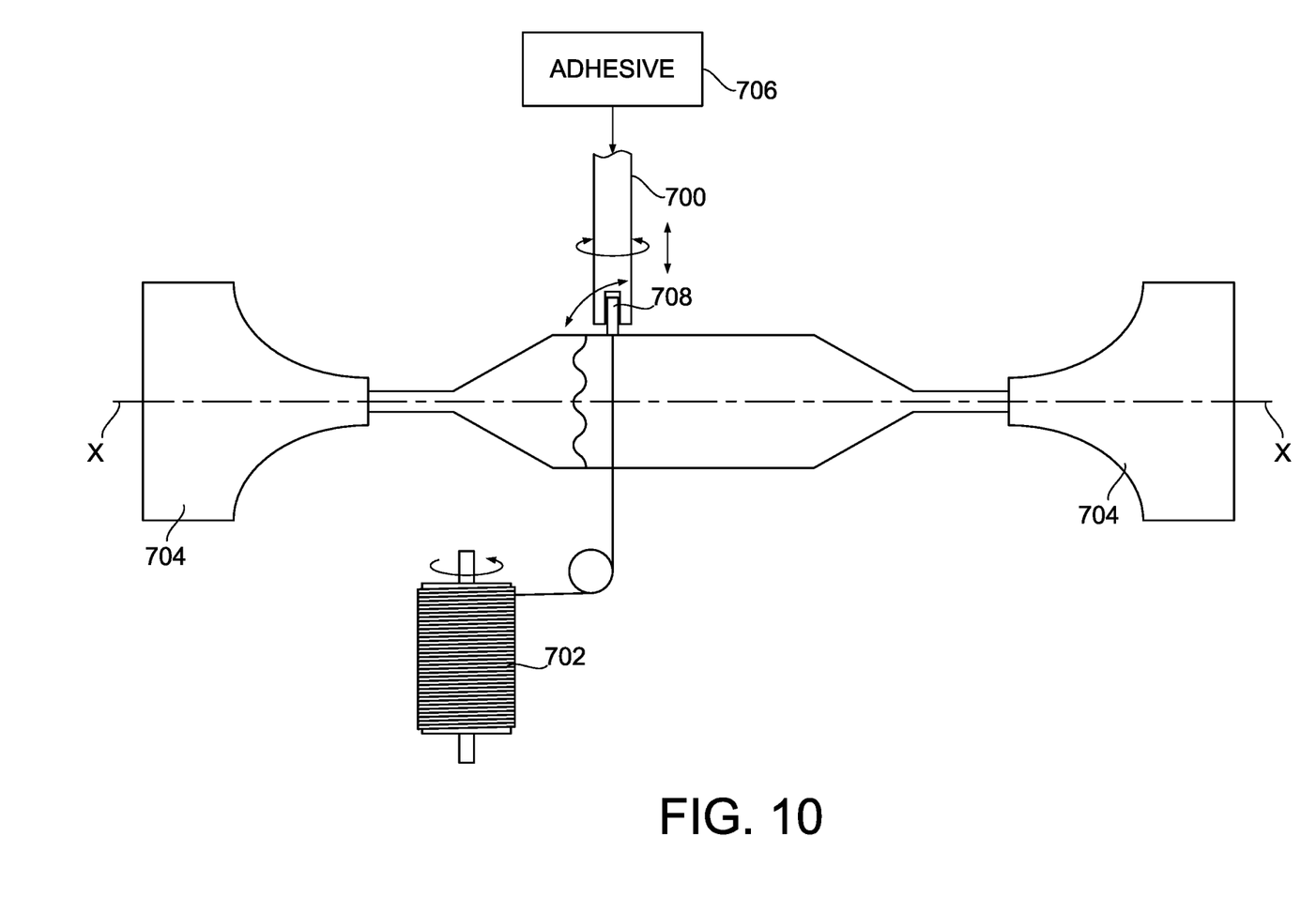
FIG. 10 schematically illustrates an apparatus for applying fibers to the balloon having a serpentine configuration.

Any of the above-mentioned fibers with S-shaped portions (repeating or otherwise) can be applied over and fixed to the base balloon using an automated applicator 700. As shown in FIG. 10, the applicator 700 may be configured to deliver the fiber from a rotatably mounted spool 702 across the surface of the balloon, which may be held in place from both ends by clamps or holders 704. Before or during the application, the fiber may be infused or coated with an adhesive, a solvent, or both. The applicator 700 can rotate and translate to position the fiber in contact with the base balloon. The applicator 700 may apply pressure normal to the surface so as to help attach the fiber to the surface upon which it is being applied and/or spread monofilaments of the fiber tow. In some embodiments, an adhesive or thermally weldable material, such as thermoplastic polyurethane (TPU), can be applied to help stick the fiber to the base balloon. The adhesive may be supplied from a reservoir 706 through a nozzle 708 adjacent the point where the fiber exits the applicator 700. In the case of a hot melt glue, both the reservoir 706 and nozzle 708 may be heated to ensure that the flowability remains good.

Further, in some embodiments, the fiber can be dipped through a solvated adhesive or thermally weldable material, such as TPU, during the application. In some embodiments, the material can be applied by spraying. In cases where both solvated thermally weldable material and thermally weldable material are used, the native thermally weldable material can advantageously meet the solvated thermally weldable material to help aid the adhesive properties. Adhesive or thermally weldable material can be applied during application of fiber or after the wind is concluded.

In any case, the fibers 134 or 142 described herein having the repeating, S-shaped portion can be laid down with minimized tooling. The process can be automated and easily updated. The fiber application process can be performed quickly, particularly the application of the strands parallel to the longitudinal axis. Further, since the path of the applicator 700 may be controlled by a computer running software, the automated process allows for ease of changeability between different size and shapes of inflatable balloons. After a base balloon is loaded, the application of all the fibers can be accomplished automatically, with no need for human intervention.

This disclosure may be considered to relate to the following items:

1. A medical apparatus, comprising:
   an inflatable balloon including at least one fiber having a portion with an S-shape in a plan view, the at least one fiber configured such that the S-shape remains and/or exists when the inflatable balloon is inflated, in particular fully inflated.

Hence, the invention concerns a medical apparatus, comprising:
   an inflatable balloon including at least one fiber having a portion with an S-shape in a plan view, in the inflated state of the balloon.

2. The medical apparatus of item 1, wherein the inflatable balloon comprises a generally cylindrical portion and first and second tapered portions connected to the generally cylindrical portion.

3. The medical apparatus of item 2, wherein only the generally cylindrical portion includes the at least one fiber having the S-shaped portion, in particular the S-shaped portion.

4. The medical apparatus of item 2, wherein only the first or second tapered portion includes the at least one fiber having the S-shaped portion, in particular the S-shaped portion.

5. The medical apparatus of any of items 1-4, wherein the at least one fiber comprises a hoop fiber extending in a circumferential direction. The S-shaped portion may extend in the circumferential direction.

6. The medical apparatus of any of items 1-4 or 5, wherein the at least one fiber comprises a longitudinal fiber extending generally parallel to a longitudinal axis of the inflatable balloon. The S-shaped portion may extend in the longitudinal direction along the longitudinal axis of the inflatable balloon.

7. The medical apparatus of any of the preceding items, wherein the at least one fiber comprises a first hoop fiber extending in a circumferential direction, and further including a longitudinal fiber extending generally parallel to a longitudinal axis, the longitudinal fiber also having an S-shaped portion.

8. The medical apparatus of any of the preceding items, wherein the at least one fiber includes a generally linear portion connected to the S-shaped portion.

9. The medical apparatus of any of the foregoing items, wherein the inflatable balloon is non-compliant.

10. The medical apparatus of any of the foregoing items, wherein the inflatable balloon comprises a base balloon to which the at least one fiber is fixedly attached by an adhesive.

11. A medical apparatus, comprising:
   an inflatable balloon including a generally cylindrical portion and first and second tapered portions connected to the generally cylindrical portion, and at least one fiber including a first portion having an S-shape, the first portion extending only along the generally cylindrical portion of the inflatable balloon.

12. The medical apparatus of item 11, wherein the at least one fiber includes a second, linear portion extending along one of the first or second tapered portions of the inflatable balloon.

13. The medical apparatus of item 11 or 12, wherein the at least one fiber comprises a hoop fiber extending in a circumferential direction.

14. The medical apparatus of any of the preceding items 11 to 13, wherein the at least one fiber comprises a longitudinal fiber extending generally parallel to a longitudinal axis of the inflatable balloon.

15. The medical apparatus of any of the preceding items 11 to 14, wherein the at least one fiber comprises a first hoop fiber extending in a circumferential direction, and further including a longitudinal fiber extending generally parallel to a longitudinal axis, the longitudinal fiber also having an S-shaped portion.

The medical apparatus of item 11 is also characterized by items 8 to 10.

16. A method of forming a medical apparatus, comprising:
fixing at least one fiber having an S-shaped portion in a plan view to an inflatable balloon,
the S-shaped portion retaining an S-shape when the inflatable balloon is fully inflated.

17. The method of item 16, wherein the fixing step comprises adhesively attaching the fiber to a base balloon.

18. The method of item 16 or 17, wherein the fixing step comprises fixing the S-shaped portion of the at least one fiber only along a generally cylindrical portion of the inflatable balloon.

19. The method of item 16, 17 or 18, wherein the fixing step is completed during a step of applying the at least one fiber.

20. The method of any of the preceding items 16 to 19, wherein the medical apparatus is the medical apparatus of any of the preceding items 1 to 15.

Each of the following terms written in singular grammatical form: "a", "an", and the ", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms parallel or perpendicular are meant to mean approximately meeting this condition, unless otherwise specified.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the inventions of this disclosure have been illustratively described and presented by way of specific exemplary embodiments, and examples thereof, it is evident that many alternatives, modifications, or/and variations, thereof, will be apparent to those skilled in the art Accordingly, it is intended that all such alternatives, modifications, or/and variations, fall within the spirit of, and are encompassed by, the broad scope of the appended claims.

The invention claimed is:

1. A medical apparatus, comprising:
an inflatable balloon defined by a balloon wall, the inflatable balloon including at least one fiber having an S-shape portion in a plan view, the S-shape remaining when the inflatable balloon is fully inflated;
wherein the S-shape portion remains at a constant radial distance from a central longitudinal axis of the balloon within a generally cylindrical portion of the balloon; and
wherein an immediately adjacent S-shaped fiber extending in the same direction as the at least one fiber does not overlap with the S-shaped portion of the at least one fiber.

2. The medical apparatus of claim 1, wherein the inflatable balloon further comprises first and second tapered portions connected to the generally cylindrical portion.

3. The medical apparatus of claim 2, wherein only the generally cylindrical portion includes the at least one fiber having the S-shaped portion.

4. The medical apparatus of claim 1, wherein the at least one fiber comprises a hoop fiber extending in a circumferential direction around a circumference of the inflatable balloon.

5. The medical apparatus of claim 1, wherein the at least one fiber comprises a longitudinal fiber extending generally parallel to a longitudinal axis of the inflatable balloon.

6. The medical apparatus of claim 1, wherein the at least one fiber comprises a first hoop fiber extending in a circumferential direction around a circumference of the balloon, and further including a longitudinal fiber extending generally parallel to a longitudinal axis, the longitudinal fiber also having an S-shaped portion.

7. The medical apparatus of claim 1, wherein the at least one fiber includes a generally linear portion connected to the S-shaped portion.

8. The medical apparatus of claim 1, wherein the inflatable balloon is non-compliant.

9. The medical apparatus of claim 1, wherein the inflatable balloon comprises a base balloon to which the at least one fiber is fixedly attached by an adhesive.

* * * * *